(12) United States Patent
Staniforth et al.

(10) Patent No.: US 8,101,160 B2
(45) Date of Patent: Jan. 24, 2012

(54) FORMULATIONS FOR USE IN INHALER DEVICES

(75) Inventors: John Nicholas Staniforth, Bath (GB); David Alexander Vodden Morton, Bath (GB)

(73) Assignee: Vectura Limited (GB)

( * ) Notice: Subject to any disclaimer, the term of this patent is extended or adjusted under 35 U.S.C. 154(b) by 209 days.

(21) Appl. No.: 10/257,883

(22) PCT Filed: Apr. 17, 2001

(86) PCT No.: PCT/GB01/01757
§ 371 (c)(1),
(2), (4) Date: Mar. 26, 2003

(87) PCT Pub. No.: WO01/78696
PCT Pub. Date: Oct. 25, 2001

(65) Prior Publication Data
US 2003/0165436 A1   Sep. 4, 2003

(30) Foreign Application Priority Data
Apr. 17, 2000 (GB) .................................. 0009468.0
Jun. 27, 2000 (EP) ..................................... 00113608

(51) Int. Cl.
*A61K 9/14* (2006.01)
*A61K 9/16* (2006.01)

(52) U.S. Cl. ............ 424/46; 424/45; 424/489; 424/490; 424/493

(58) Field of Classification Search .................. 424/400, 424/434, 489, 490, 43, 46, 45, 493; 514/951
See application file for complete search history.

(56) References Cited

U.S. PATENT DOCUMENTS

| | | | |
|---|---|---|---|
| 4,349,542 A * | 9/1982 | Staniforth | 424/679 |
| 5,478,578 A | 12/1995 | Arnold et al. | |
| 5,612,053 A * | 3/1997 | Baichwal et al. | 424/440 |
| 6,153,224 A * | 11/2000 | Staniforth | 424/490 |
| 6,528,096 B1 * | 3/2003 | Musa et al. | 424/490 |
| 6,645,466 B1 | 11/2003 | Keller et al. | |

FOREIGN PATENT DOCUMENTS

| | | | |
|---|---|---|---|
| CA | 2 195 065 | | 2/1996 |
| EP | 0663815 | | 7/1995 |
| WO | WO9311746 | | 12/1992 |
| WO | WO9511666 | | 10/1994 |
| WO | WO9602231 | | 6/1995 |
| WO | WO 96/02231 | | 2/1996 |
| WO | WO 95/11666 | * | 5/1996 |
| WO | WO 96/23485 | | 8/1996 |
| WO | WO 9623485 | * | 8/1996 |
| WO | WO0028979 | | 11/1999 |

OTHER PUBLICATIONS

Lucas P. et al., "Protein Deposition from Dry Powder Inhalers: Fine Particle Multiplets as Performance Modifiers." Pharm. Research, vol. 15, No. 4; Apr. 1998 pp. 562-569.
Kawashima Y. et al., "Effect of Surface Morphology of Carrier Lactose on Dry Powder Inhalation Property of Pranlukast Hydrate." International Journal of Pharmaceutics, vol. 172, No. 1-2; Oct. 15, 1998 pp. 179-188.
Y. Kawashima et al., 'Effect of surface morphology of carrier lactose on dry powder inhalation property of pranlukast hydrate' Int. J. Pharmac. 172,179-188 (1998).
Excerpt from N. M. Kassem, 'Generation of deeply inspirable clouds from dry powder mixtures' Department of Pharmacy, King's College University of London (1990).
Notice of Opposition to European Patent No. EP 1 276 474, 'Formulations for Use in Inhaler Devices' along with Annex to the Notice of Opposition, 2008.
X. M. Zeng et al. "Effects of particle size and adding sequence of fine lactose on the deposition of salbutamol sulphate from a dry powder formulation" International Journal of Pharmaceutics 182 p. 133-144 (1999)t.
F. Podczeck "Particle-particle Adhesion in Pharmaceutical Powder Handling" Imperial College Press; p. 95-97 (1998).
S. Budavari et al. "The Merck Index: an Encyclopedia of Chemicals, Drugs, and Biologicals" Merck & Co. Inc. p. 843 (1989).
C. A. Dunbar et al. "Dispersion and Characterization of Pharmaceutical Dry Powder Aerosols" Kona No. 16, p. 7-44 (1998).
M. Zeng et at. "Particulate Interactions in Dry Powder Formulations for Inhalation", King's College London, p. 165-167 (2001).
Grounds of Appeal submitted by Opponent dated Apr. 28, 2011 in connection with European Patent No. 1,276,474.
Grounds of Appeal submitted by Patentee dated Apr. 28, 2011 in connection with European patent No. 1,276,474.
Further comments by Opponent dated Sep. 10, 2009 in connection with European patent No. 1,276,474.
Response to Opposition dated Dec. 8, 2008 in connection with European patent No. 1,276,474.
Notice of Opposition dated Mar. 12, 2008 in connection with European patent No. 1,276,474.
Statement of Opposition dated Mar. 12, 2008 in connection with European patent No. 1,276,474.

* cited by examiner

*Primary Examiner* — Mina Haghighatian
(74) *Attorney, Agent, or Firm* — Davidson, Davidson & Kappel

(57) ABSTRACT

A formulation for use in an inhaler device comprises carrier particles having a diameter of at least 50 μm and a mass median diameter of at least 175 μm; fine particles of an excipient material having a mass median aerodynamic diameter of not more than 20 μm; and active particles. The formulation has excellent flowability even at relatively high contents of fine particles.

42 Claims, 4 Drawing Sheets

FORMULATIONS FOR USE IN INHALER DEVICES

Figure 1:
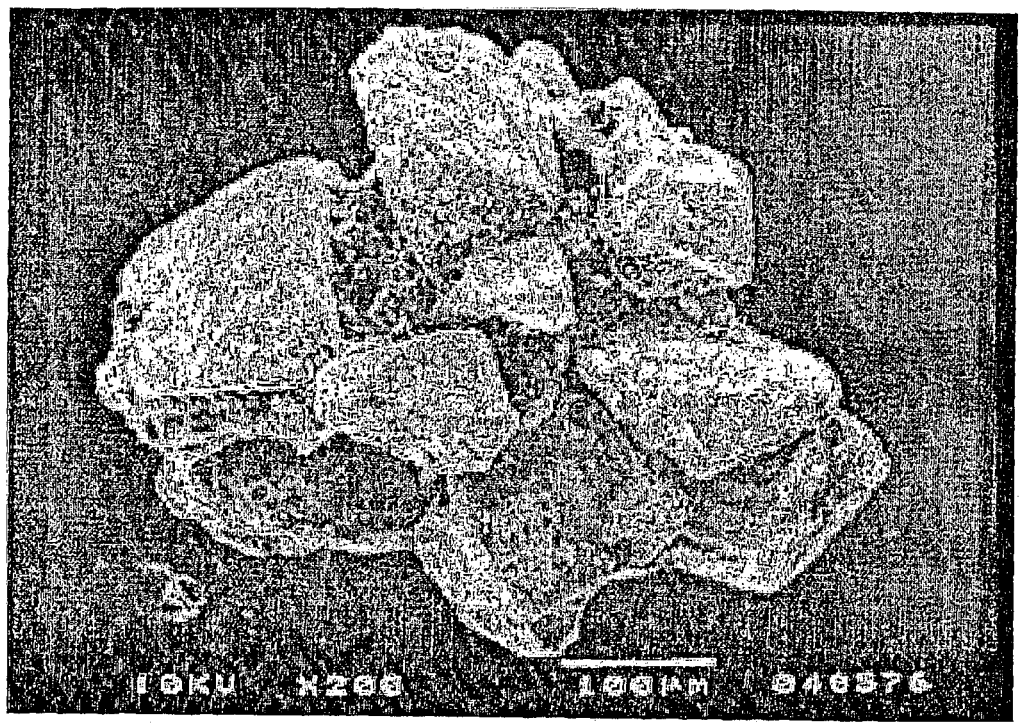
Figure 2:
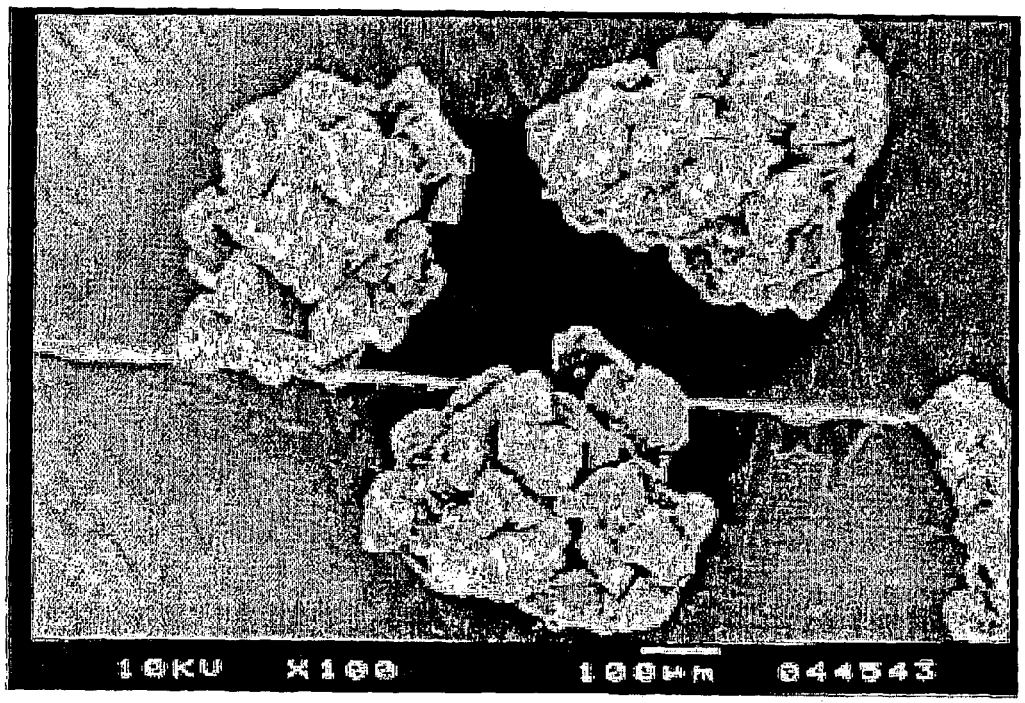
Figure 3:
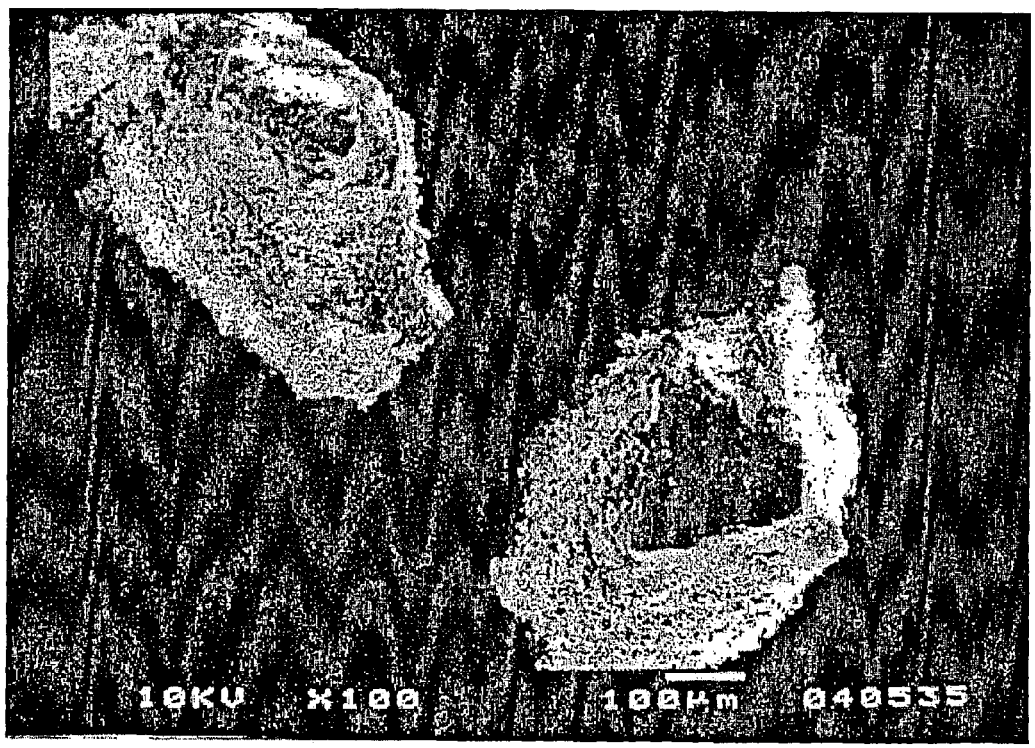
Figure 4:
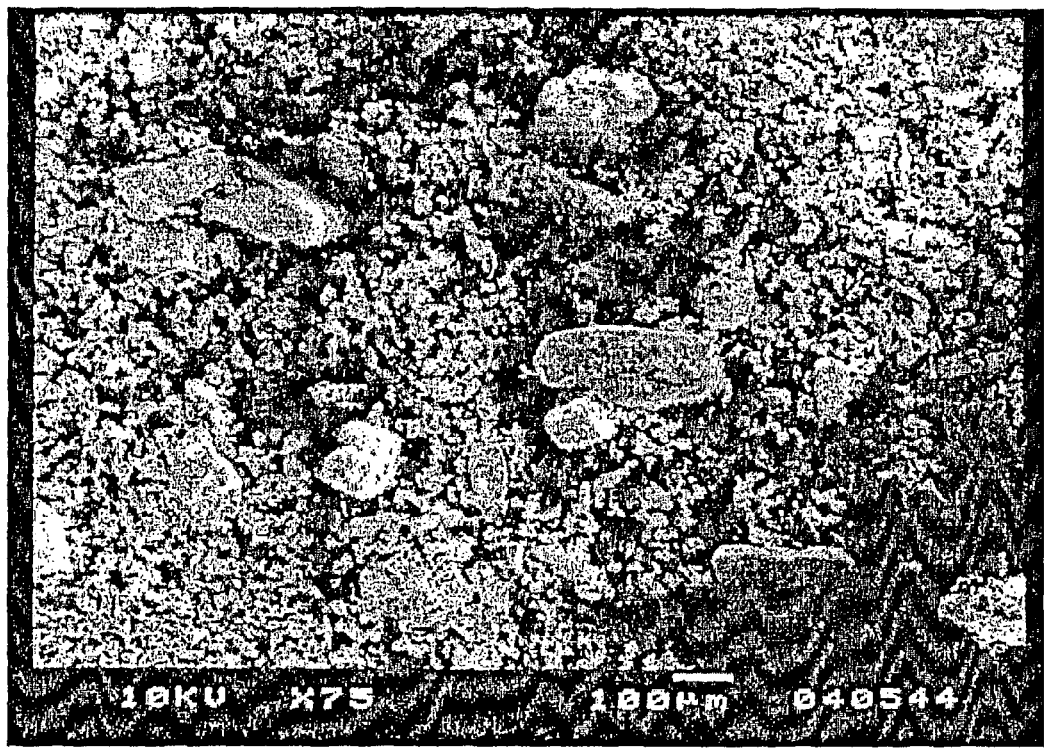

The invention relates to carrier materials for use in inhaler devices, to formulations comprising the carrier materials and to the use of the formulations.

The administration of pharmacologically active agents by inhalation is a widely used technique, especially for the treatment of diseases of the respiratory tract. The technique is also used for the administration of certain active agents having systemic action, which are absorbed, via the lungs, into the bloodstream. Known inhaler devices include nebulizers, pressurised metered dose inhalers and dry powder inhalers. The present invention is primarily concerned with formulations for use in dry powder inhalers, although in some circumstances formulations according to this invention may also or instead be useful in pressurised metered dose inhalers.

The delivery of dry powder particles of an active agent to the respiratory tract presents certain problems. The inhaler should deliver to the lungs the maximum possible proportion of the active particles, expelled from the device, including a significant proportion to the lower lung, preferably even at the poor inhalation capabilities of some patients, especially asthmatics. In use of many of the currently available devices, however, only a proportion, and frequently as little as 10%, of the active particles expelled from the device on inhalation reach the lower lung.

On exit from the inhaler device, the active particles should form a physically and chemically stable aerocolloid which remains in suspension until it reaches an alveolar or other absorption site. Once at the absorption site, the active particles should be capable of efficient collection by the pulmonary mucosa with no active particles being exhaled from the absorption site.

The size of the active particles is important. For effective delivery of active particles deep into the lungs, the active particles should be small, with an equivalent aerodynamic diameter substantially in the range of up to 10 µm. Small particles are however thermodynamically unstable due to their high surface area to volume ratio, which provides significant excess surface free energy and encourages particles to agglomerate. Agglomeration of small particles in the inhaler and adherence of particles to the walls of the inhaler can result in the active particles leaving the inhaler as large agglomerates or in their not leaving the inhaler and remaining adhered to the interior thereof.

The uncertainty as to the extent of agglomeration of the particles between each actuation of the inhaler and between different inhalers and different batches of particles, leads to poor dose reproducibility. It has been found that powders are generally reproducibly fluidisable, and therefore reliably removable from an inhaler device, when the particles have a diameter greater than 60 µm. Good flow properties are desirable in the contexts of metering and of dispersal from the device.

To give the most effective dry powder aerosol, therefore, the particles should be large while in the inhaler, but small when in the respiratory tract.

It is common, in an attempt to achieve those demands, to include in the dry powder formulation carrier particles, to which the active particles can adhere whilst in the device, the active particles then being dispersed from the surfaces of the carrier particles on inhalation into the respiratory tract, to give a fine suspension. It is known that the presence of a certain amount of fine excipient material, normally of the same material as the carrier, can improve the proportion of drug reaching the lung. The presence of such a fraction of fine excipient is conventionally limited to less than 10% and generally less than 5% due to the catastrophic loss of flowability at higher fine particle contents, leading to poor dose reproducibility.

The invention provides a formulation for use in an inhaler device, comprising carrier particles and having a diameter of at least 50 µm and a mass median aerodynamic diameter of at least 175 µm;
fine particles of an excipient material having a mass median aerodynamic diameter of not more than 20 µm; and active particles.

The formulation of the invention surprisingly has both excellent flowability within the device and, on expulsion from the device, permits good dispersion of the active particles from the carrier particles and generation of a relatively high fine particle fraction, promoting delivery of a relatively large proportion of the active particles into the lung.

The use of carrier particles of relatively large size is described in WO96/02231, but that document does not suggest the incorporation of fine particles of excipient. EP 0663815B describes a formulation comprising an excipient mixture having a fine fraction and a coarser fraction, but suggests that the average particle size of the coarser fraction should be below 150 µm. In contrast, the carrier particles used in accordance with the present invention have a mass median aerodynamic diameter (MMAD) of at least 175 µm. In fact, it is preferred that the MMAD of the carrier particles is at least 200 µm.

The carrier particles have an aerodynamic diameter of not less than 50 µm. Advantageously, not more than 10% by weight, and preferably not more than 5% by weight, of the carrier particles have an aerodynamic diameter of 150 µm or less. Advantageously at least 90% by weight of the carrier particles have a diameter of 175 µm or more, and preferably 200 µm or more. Advantageously, at least 90% by weight, and preferably at least 95% by weight, of the carrier particles have a diameter of not more than 1 mm. Preferably at least 90% by weight of the carrier particles have a diameter of not more than 600 µm. Advantageously, at least 50% by weight, and preferably at least 60% by weight, of the carrier particles have a diameter of 200 µm or more. Preferably, at least 90% by weight of the carrier particles have a diameter between 150 µm and 750 µm, more preferably between 150 µm and 650 µm. Particular advantages are offered by formulations in which substantially all of the carrier particles have a diameter in the range of about 210 to about 360 µm or from about 350 to about 600 µm.

The fine excipient particles may have an aerodynamic diameter of less than 50 µm. Advantageously, at least 90% by weight of the fine excipient particles have an aerodynamic diameter of not more than 40 µm. The excipient particles advantageously have an MMAD of not more than 20 µm, preferably of not more than 15 µm, and more preferably not more than 10 µm, especially not more than 8 µm. The MAD of the excipient particles will generally be not less than 0.1 µm, for example not less than 1 µm.

The fine excipient particles may be present in an amount of 0.1 to 50% or in an amount of 9 to 50%, and advantageously from 0.2 to 50%, preferably from 1 to 20%, by weight based on the total weight of the carrier particles, fine excipient particles and active particles. Preferably, the fine excipient particles are present in an amount of not less than 4% by weight, more preferably not less than 5% by weight, based on the total weight of the formulation up to 15% by weight based on the total weight of the formulation.

The carrier particles may be of any acceptable pharmacologically inert material or combination of materials. For example, the carrier particles may be composed of one or more materials selected from sugar alcohols; polyols, for example sorbitol, mannitol and xylitol, and crystalline sugars, including monosaccharides and disaccharides; inorganic salts such as sodium chloride and calcium carbonate; organic salts such as sodium lactate; and other organic compounds such as urea, polysaccharides, for example starch and its derivatives; oligosaccharides, for example cyclodextrins and dextrins. Advantageously the carrier particles are of a crystalline sugar, for example, a monosaccharide such as glucose or arabinose, or a disaccharide such as maltose, saccharose, dextrose or lactose. Preferably, the carrier particles are of lactose.

The fine particles of excipient material may be of a substantially pharmacologically inert material. The excipient material may be any substantially inert material that is suitable for use as an excipient in an inhalable formulation. The excipient material preferably comprises one or more crystalline sugars, for example, dextrose and/or lactose. Most preferably the excipient material consists essentially of lactose.

Advantageously, the fine excipient particles are of the same material as the carrier particles. It is especially preferred for the carrier particles and the fine excipient particles to be of lactose. Where, as is preferred, the carrier particles and the fine excipient particles are of the same compound, for example, lactose, it may be found convenient to consider all the particles of that compound having an aerodynamic diameter of less than 50 μm to be fine excipient particles, whilst particles of aerodynamic diameter of 50 μm or more are regarded as carrier particles.

The carrier particles are preferably of a material having a fissured surface, that is, on which there are clefts and valleys and other recessed regions, referred to herein collectively as fissures. The fissures should preferably be at least 5 μm wide extending to at least 5 μm deep, preferably at least 10 μm wide and 10 μm deep and most preferably at least 20 μm wide and 20 μm deep.

Because of the excellent flow properties of the formulations containing the fissured carrier particles, the formulations offer special advantages in the administration of active agents to be administered in relatively large doses. Thus, whereas formulations containing conventional lactose carriers and fine particle contents of above 5% tend to have poor flow properties, with flow properties at fine particle contents above 10% being very poor, the formulations of the invention may have adequate flow properties even at fines contents (that is contents of active particles and of any fine particles of excipient material, together with any other particles of aerodynamic diameter of not more than 20 μm) of up to 90% by weight, based on the total weight of fines and carrier particles. Moreover, the fissured carrier particles offer particular advantages in that they are capable of retaining relatively large amounts of fine material in the fissures without or with only little segregation. That is thought to underly the good respirable, fraction that is generated in use of the formulations. Advantageously, the fines content is not more than 50% by weight, and more preferably not more than 20% by weight, based on the total weight of fines and carrier particles. Preferably, the fines content is at least 5% by weight, based on the total weight of fines and carrier particles. The invention offers particular advantages in the case of formulations containing at least 10%, for example, from 10 to 20% by weight fines or at least 20%, for example from 20 to 50% by weight fines, in each case, based on the total weight of fines and carrier particles. The fines content may include from 0.1 to 90% by weight active particles, for example from 0.1 to 80% by weight, and advantageously from 0.1 to 70% by weight active particles, in each case based on the total weight of fines. In many cases, however, the active particles will constitute less than half of the total weight of fines.

A number of methods may be used to determine whether carrier particles have a fissured surface that will offer the above-mentioned capability of retaining relatively large fines contents substantially without segregation:

1. Determination of tapped density.

The tapped density of the fissured carrier particles may be about 6% or more, and preferably 15% or more, lower than the tapped density of carrier particles of the same material and of particle characteristics of a kind typical of carrier particles which have conventionally been used in the manufacture of inhalable powders. In the case of fissured carrier particles of crystalline sugars, for example lactose, the tapped density of the fissured particles is not more than 0.75 g/cm$^3$, and preferably not more than 0.70 g/cm$^3$. The tapped density of lactose grades conventionally used in the manufacture of commercial DPI formulations is typically about 0.8 g/cm$^3$. Tapped densities referred to herein may be measured as follows:

A measuring cylinder is weighed on a top pan balance (2 place). Approximately 50 g powder is introduced into the measuring cylinder, and the weight is recorded. The measuring cylinder containing the powder is attached to a jolting volumeter (Jel Stampfvolumeter). The jolting volumeter is set to tap 200 times. During each tap, the measuring cylinder is raised and allowed to fall a set distance. After the 200 taps, the volume of the powder is measured. The tapping is repeated and the new volume measured. The tapping is continued until the powder will settle no more. The tapped density is calculated as the weight of the powder divided by the final tap volume. The procedure is performed three times (with new powder each time) for each powder measured, and the mean tapped density calculated from those three final tapped volume values.

2. Mercury Intrusion Porosimetry. Mercury intrusion porosimetry assesses the pore size distribution and the nature of the surface and pore structure of the particles. Porosimetry data is suitably collected over pressure range 3.2 kPa to 8.7 MPa, for example, using an Autopore 9200 II Porosimeter (Micromeritics, Norcross, USA). Samples should be evacuated to below 5 Pa prior to analysis to remove air and loosely bound surface water. Suitable lactose is characterised by a bulk density of not more than 0.65 g/cm$^3$ and preferably not more than 0.6 g/cm$^3$. Suitable lactose is also characterised by a total intrusion volume measured by mercury intrusion porosimetry of at least 0.8 cm$^3$ g$^{-1}$ and preferably at least 0.9 cm$^3$ g$^{-1}$. (It has been found that lactose having a bulk density of 0.6 g/cm$^3$ as measured by mercury intrusion porosimetry has a tapped density of about 0.7 g/cm$^3$, whereas the discrepancy between the two methods at lower densities is less.)

3. "Fissure Index". The term "fissure index" used herein refers to the ratio of a theoretical envelope volume of the particles, as calculated from the envelope of the particles, to the actual volume of the particles, that is, omitting fissures within the envelope. Suitable, particles are those having a fissure index of at least 1.25. The theoretical envelope volume may be determined optically, for example, by examining a small sample of the particles using an electron microscope. The theoretical envelope volume of the particles may be estimated via the following method. An electron micrograph of the sample may be divided into a number of grid squares of approximately equal populations, each containing a representative sample of the particles. The population of one or more grids may then be examined and the envelope encompassing each of the particles determined visually as follows. The Feret's diameter for particles within a grid is measured relative to a fixed axis of the image. Typically at least ten particles are measured for their Feret's diameter. Feret's diameter is defined as the length of the projection of a particle along a given reference line as the distance between the extreme left and right tangents that are perpendicular to the reference line. A mean Feret's diameter is derived. A theoretical mean envelope volume may then be calculated from this mean diameter to give a representative value for all the grid squares and thus the whole sample. Division of that value by the number of particles gives the mean value per particle. The actual volume of the particles may then be calculated as follows. First, the mean mass of a particle is calculated. A sample of approximately 50 mg is taken and its precise weight recorded to 0.1 mg. Then by optical microscopy the precise number of particles in that sample is determined. The mean mass of one particle can then be determined. The procedure is then repeated five times to obtain a mean value of this mean. Second, a fixed mass of particles (typically 50 g), is weighed out accurately, and the number of particles within this mass is calculated using the above mean mass value of one particle. Finally, the sample of particles is immersed in a liquid in which the particles are insoluble and, after agitation to remove trapped air, the amount of liquid displaced is measured. From this the mean actual volume of one particle can be calculated. The fissure index is advantageously not less than 1.5, and is, for example, 2 or more.

4. "Rugosity Coefficient". The rugosity coefficient is used to mean the ratio of the perimeter of a particle outline to the perimeter of the 'convex hull'. This measure has been used to express the lack of smoothness in the particle outline. The 'convex hull' is defined as a minimum enveloping boundary fitted to a particle outline that is nowhere concave. (See "The Shape of Powder-Particle Outlines" A. E. Hawkins, Wiley.) The 'rugosity coefficient' may be calculated optically as follows. A sample of particles should be identified from an electron micrograph as identified above. For each particle the perimeter of the particle outline and the associated perimeter of the 'convex hull' is measured to provide the rugosity coefficient. This should be repeated for at least ten particles to obtain a mean value. The mean rugosity coefficient is at least 1.25.

Carrier particles which have the above-mentioned capability of retaining relatively large amounts of fine material without or with only little segregation will generally comply with all of Methods 1 to 4 above, but for the avoidance of doubt any carrier particles which comply with at least one of Methods 1 to 4 is deemed to be a fissured particle.

The carrier particles are advantageously in the form of an agglomerate consisting of a plurality of crystals fused to one another, the fastness of agglomeration being such that the carrier particles have substantially no tendency to disintegrate on expulsion from the inhaler device. In the case of crystalline sugars, such as lactose, such structures may be obtained in a wet granulation process, in which crystals within an agglomerate become fused to one another by solid bridges, the resultant structure having a complex shape of high irregularity and/or high fractal dimension, including a multiplicity of clefts and valleys, which in some cases may be relatively deep. Each agglomerate will generally contain at least three lactose primary crystals of the characteristic tomahawk shape.

Suitably shaped carrier particles also include dendritic spherulites of the type disclosed in U.S. Pat. No. 4,349,542 for use in tablet manufacture. The carrier particles advantageously constitute at least 50%, preferably at least 60% and especially at least 70% by weight of the formulation.

The active particles referred to throughout the specification will comprise an effective amount of at least one active agent that has therapeutic activity when delivered into the lung. The active particles advantageously consist essentially of one or more therapeutically active agents. Suitable therapeutically active agents may be drugs for therapeutic and/or prophylactic use. Active agents which may be included in the formulation include those products which are usually administered orally by inhalation for the treatment of disease such a respiratory disease, for example, β-agonists.

The active particles may comprise at least one $β_2$-agonist, for example one or more compounds selected from terbutaline, salbutamol, salmeterol and formoterol. If desired, the active particles may comprise more than one of those active agents, provided that they are compatible with one another under conditions of storage and use. Preferably, the active particles are particles of salbutamol sulphate. References herein to any active agent are to be understood to include any physiologically acceptable derivative. In the case of the $β_2$-agonists mentioned above, physiologically acceptable derivatives include especially salts, including sulphates.

The active particles may be particles of ipatropium bromide.

The active particles may include a steroid, which may be beclometasone dipropionate or may be fluticasone. The active principle may include a cromone which may be sodium cromoglycate or nedocromil. The active principle may include a leukotriene receptor antagonist.

The active particles may include a carbohydrate, for example heparin.

The active particles may advantageously comprise a therapeutically active agent for systemic use provided that that agent is capable of being absorbed into the circulatory system via the lungs. For example, the active particles may comprise peptides or polypeptides or proteins such as DNase, leukotrienes or insulin (including substituted insulins and pro-insulins), cyclosporin, interleukins, cytokines, anti-cytokines and cytokine receptors, vaccines (including influenza, measles, 'anti-narcotic' antibodies, meningitis), growth hormone, leuprolide and related analogues, interferons, desmopressin, immunoglobulins, erythropoeitin, calcitonin and parathyroid hormone. The formulation of the invention may in particular have application in the administration of insulin to diabetic patients, thus avoiding the normally invasive administration techniques used for that agent.

The formulations of the invention may advantageously be for use in pain relief. Non-opioid analgesic agents that may be included as pain relief agents are, for example, alprazolam, amitriptyline, aspirin, baclofen, benzodiazepines, bisphosphonates, caffeine, calcitonin, calcium-regulating agents, carbamazepine, clonidine, corticosteroids, dantrolene, dexamethasone, disodium pamidronate, ergotamine, flecainide, hydroxyzine, hyoscine, ibuprofen, ketamine, lignocaine, lorazepam, methotrimeprazine, methylprednisolone, mexiletine, mianserin, midazolam, NSAIDs, nimodipine, octreotide, paracetamol, phenothiazines, prednisolone, somatostatin. Suitable opioid analgesic agents are: alfentanil hydrochloride, alphaprodine hydrochloride, anileridine, bezitramide, buprenorphine hydrochloride, butorphanol tartrate, carfentanil citrate, ciramadol, codeine, dextromoramide, dextropropoxyphene, dezocine, diambrphine hydrochloride, dihydrocodeine, dipipanone hydrochloride, enadoline, eptazocine hydrobromide, ethoheptazine citrate, ethylmorphine hydrochloride, etorphine hydrochloride, fentanyl citrate, hydrocodone, hydromorphone hydrochloride, ketobemidone, levomethadone hydrochloride, levomethadyl acetate, levorphanol tartrate, meptazinol hydrochloride, methadone hydrochloride, morphine, nalbuphine hydrochloride, nicomorphine hydrochloride, opium, hydrochlorides of mixed opium alkaloids, papaveretum, oxycodone, oxymorphone hydrochloride, pentamorphone, pentazocine, pethidine hydrochloride, phenazocine hydrobromide, phenoperidine hydrochloride, picenadol hydrochloride, piritramide, propiram furmarate, remifentanil hydrochloride, spiradoline mesylate, sufentanil citrate, tilidate hydrochloride, tonazocine mesylate, tramadol hydrochloride, trefentanil.

The technique could also be used for the local administration, of other agents for example for anti cancer activity, anti-virals, antibiotics, muscle relaxants, antidepressants, antiepileptics or the local delivery of vaccines to the respiratory tract.

The active particles advantageously have a mass median aerodynamic diameter (MMAD) in the range of up to 15 μm, for example 0.01 to 15 μm, preferably from 0.1 to 10 μm, and most preferably from 1 to 9 μm, for example, from 1 to 8 μm. The active particles are present in an effective amount, for example, at least 0.01% by weight, and may be present in an amount of up to 90% by weight, based on the total weight of carrier particles, fine excipient particles and active particles. Advantageously, the active particles are present in an amount not exceeding 60% by weight based on the total weight of carrier particles, fine excipient particles and active particles.

It will be appreciated that the proportion of active agent present will be chosen according to the nature of the active agent. In many cases, it will be preferred for, the active agent to constitute no more than 10%, more preferably no more than 5%, and especially no more than 2% by weight based on the total weight of carrier particles, fine excipient particles and active particles.

The advantageous flow properties of formulations of the invention may be demonstrated, for example, using a Flodex Tester, which can determine a flowability index over a scale of 4 to 40 mm, corresponding to a minimum orifice diameter through which smooth flow of the formulation occurs in the Tester. The flowability index, when so measured, of formulations of the invention containing fissured lactose will generally be below 12 mm, even where fine particle Contents (that is, particles of aerodynamic diameter less than 50 μm or preferably less than 20 μm) exceed 10% by weight of the formulation.

The invention provides a formulation for use in a dry powder inhaler, comprising more than 5%, and preferably more than 10% by weight, based on the total weight of the formulation, of particles of aerodynamic diameter less than 20 μm, the formulation having a flowability index of 12 mm or less. The term "flowability index" as used herein refers to flowability index values as measured using a Flodex Tester.

In addition to the carrier particles, active particles and fine excipient particles, the formulation may comprise one or more additives suitable for use in inhaler formulations, for example, flavourings, lubricants, and flow improvers. Where such additives are present, they will generally not exceed 10% by weight of the total weight of the formulation.

The formulation may be a powder formulation for use in a dry powder inhaler. The formulation may be suitable for use in a pressurised metered dose inhaler. The formulations of the invention are particularly suitable for use in dry powder inhalers of the kind which offer low resistance to inhalation by the user or which have high turbulence or high deaggregation efficiency.

Certain embodiments of the invention will now be described in detail with reference to the accompanying illustrations in which:

FIG. 1 is a scanning electron micrograph (SEM) of a relatively highly fissured lactose particle;

FIG. 2 is an SEM at lower magnification than FIG. 1 showing a number of lactose particles of the kind shown in FIG. 1 at lower magnification;

FIG. 3 is an SEM of particles of a formulation according to the invention; and FIG. 4 is an SEM of a formulation containing conventional lactose carrier particles and fines.

With reference to FIG. 1, it may be seen that the lactose particle shown consists of a number of individual lactose crystals which are fused to one another. The crystals define between them at the surface, of the particle a multiplicity of relatively deep fissures or crevices. Such particles are known and have previously been regarded as suitable for use in tablet manufacture. Surprisingly, it has been found that lactose particles such as that shown in FIG. 1 may be used as carrier particles and are able to enhance the delivery of an active substance to the lung, that is, to increase the fine particle fraction. The active substance and the fine excipient tend because of their small particle size and consequent high surface energy to adhere to the larger lactose particles. Adhesion occurs predominantly within the fissures and crevices. Due to the optimum width, depth and shape of the fissures, the resultant loaded carrier particles have good stability against deagglomeration within the inhaler device and yet permit effective dispersion of the active particles and fine excipient on expulsion from the device after actuation.

FIG. 2 shows a group of lactose particles similar to that of FIG. 1.

Referring to FIGS. 3 and 4, the lactose carrier particle of FIG. 3 holds the fine material within the fissures of its agglomerated structure, whilst in the conventional formulation of FIG. 4 much of the fine material is not adhered to the conventional lactose carrier particles. Conventional carrier particles are typically crystals which have the characteristic tomahawk shape of lactose crystals. They may also be amorphous in shape, but rarely consist of more than two fused crystals. Thus the conventional carrier particles are substantially without the clefts and valleys of the fissured particles used in accordance with the present invention.

References herein to a "diameter" in relation to carrier particles means the diameter determined using laser diffraction, for example, using a Malvern Mastersizer, and references herein to a "mass median diameter" in relation to carrier particles is to be interpreted accordingly.

It may be found convenient to determine the diameters of particles in a formulation according to the invention by dispersing the particles in a liquid that does not dissolve any of the component particles, sonicating to ensure complete dispersion, and analysing the dispersion by means of laser diffraction, for example using a Malvern Mastersizer. That method will be suitable where separate analysis of fine particles of different materials is unnecessary.

In practice, it may be desired to examine a larger particle size fraction separately from a smaller size fraction. In that case, an air jet sieve may be used to effect separation. A mesh corresponding to the desired diameter at which the separation is to be effected is then used in the air jet sieve. A mesh corresponding to a diameter of 50 μm may thus be used for separation, larger particles being retained by the sieve whilst smaller particles pass through to be collected on a filter. That enables different techniques to be applied to analysis of the larger particles (≧50 μm) and the smaller particles (<50 μm) if desired.

In the case of particles of the size of the carrier particles used in accordance with the invention, the diameter as measured using laser diffraction approximates the aerodynamic diameter. If preferred, therefore, the aerodynamic diameters of the carrier particles may be determined and the mass median aerodynamic diameter (MMAD) calculated therefrom.

MMADs referred to herein in relation to fine excipient particles and active particles may be measured using any suitable technique, for example, using an impactor such as a cascade impactor, and analysing the size fractions so obtained, for example using HPLC.

Alternatively, respective samples of the formulation may each be treated with a solvent that is known to dissolve one or more, but not all, of the ingredients and examining the undissolved particles by any suitable method, for example, laser diffraction.

The following Examples illustrate the invention.

EXAMPLE 1

20 g of Microfine lactose (Borculo—MMAD about 8 μm) was placed in a high shear blender with 20 g of micronised Salbutamol Sulphate (MMAD about 2 μm). The mixture was blended for 5 minutes.

8 g of sieved Prismalac (trade mark) lactose was weighed into a glass vessel. Prismalac lactose is sold in the UK by Meggle for use in tablet manufacture. The lactose, as purchased had been sieved on a stack of sieves in order to recover the sieve fraction passing through a 600 μm mesh sieve, but not passing through a 355 μm mesh sieve. That fraction is referred to below as 355-600 Prismalac.

2 g of the lactose fines and micronised salbutamol sulphate blend was added to the 355-600 Prismalac in the glass vessel. The glass vessel was sealed and the vessel located in a "turbula" tumbling blender. The vessel and contents were tumbled for approximately 15 minutes at a speed of 42 RPM.

The formulation so obtained was loaded into size 3 gelatin capsules at 20 mg per capsule. The loaded capsules were rested for a period of 24 hours. Three capsules were then fired from a Cyclohaler sequentially into a Twin Stage Impinger at a flow rate of 60 liters per minute, with a modified stage 1 jet of 12.5 mm internal diameter, which was estimated to produce a cut-off diameter of 5.4 μm. The operation of the Twin Stage Impinger is described in WO95/11666. Modification of a conventional Twin Stage Impinger, including the use of modified stage 1 jets, is described by Halworth and Westmoreland (J. Pharm. Pharmacol. 1987, 39:966-972). Below, the "fine particle fraction" is the proportion of the drug emitted from the inhaler device into the Impinger which reaches stage 2 of the Impinger.

The composition Of the formulation is summarised in Table 1.

TABLE 1

|  | Example 1 |  | Comparison |
| --- | --- | --- | --- |
| 355-600 Prismalac lactose | 4 g | 80% | 8 g |
| Salbutamol sulphate | 0.5 g | 10% | 1 g |
| Microfine lactose | 0.5 g | 10% | — |
| Fine particle fraction |  | 40% | 10% |

As shown in Table 1, the fine particle fraction is improved in the presence of fine lactose. On omission of the Prismalac from the ingredients of Example 1, the formulation was found to have very poor flow properties, preventing reliable and reproducible metering. As a result, the fine particle fraction was found to be very variable.

EXAMPLE 2

Example 1 was repeated using micronised budesonide (MMAD 2 μm) in place of salbutamol sulphate, and a fine particle fraction of about 40% was obtained.

EXAMPLE 3

Example 1 was repeated using micronised insulin and similar results were obtained to those of Example 1.

The invention claimed is:

1. A formulation for use in an inhaler device, comprising carrier particles in the form of an agglomerate consisting of a plurality of crystals fused to one another, wherein the carrier particles have a diameter of at least 50 μm and a mass median aerodynamic diameter of at least 175 μm and a fissured surface in which the fissures between the crystals of the agglomerate are at least 20 μm wide and at least 20 μm deep;

fine particles consisting of an excipient material consisting of one or more crystalline sugars and having a mass median aerodynamic diameter of not more than 20 μm; and active particles; wherein the fine excipient particles are present in an amount of from not less than 5% by weight based on the total weight of the formulation, to 50% by weight based on the total weight of the carrier particles, fine excipient particles and active particles.

2. A formulation according to claim 1, in which the mass median diameter of the carrier particles is at least 200 μm.

3. A formulation according to claim 1, in which the mass median aerodynamic diameter of the fine excipient particles is not more than 15 μm.

4. A formulation according to claim 3, in which the mass median aerodynamic diameter of the fine excipient particles is not more than 10 μm.

5. A formulation according to claim 1, in which the carrier particles and the fine excipient particles are of the same material.

6. A formulation according to claim 1, in which at least the carrier particles are of a crystalline sugar.

7. A formulation according to claim 6, in which the carrier particles are of dextrose or lactose.

8. A formulation according to claim 7, in which the carrier particles are of lactose.

9. A formulation according to claim 1, in which the fine excipient particles are of dextrose or lactose.

10. A formulation according to claim 9, in which the fine excipient particles are of lactose.

11. A formulation according to claim 1, in which the carrier particles are of a crystalline sugar having a tapped density not exceeding 0.75 g/cm$^3$.

12. A formulation according to claim 1, in which the carrier particles have a tapped density not exceeding 0.70 g/cm$^3$.

13. A formulation according to claim 1, in which the carrier particles have a bulk density as measured by mercury intrusion porosimetry of not exceeding 0.6 g/cm3.

14. A formulation according to claim 1, in which the carrier particles are obtainable by a wet granulation process.

15. A formulation according to claim 1, in which the carrier particles are dendritic spherulites.

16. A formulation according to claim 1, which contains up to 90% by weight of active particles and fine excipient particles, based on the total weight of active particles, fine excipient particles and carrier particles.

17. A formulation according to claim 16, which contains up to 50% by weight of active particles and fine excipient particles, based on the total weight of active particles, fine excipient particles and carrier particles.

18. A formulation according to claim 17, which contains up to 20% by weight of active particles and fine excipient particles, based on the total weight of active particles, fine excipient particles and carrier particles.

19. A formulation according to claim 1, in which the active particles are present in an amount of from 0.01 to 90% by weight, based on the total weight of active particles and fine excipient particles.

20. A formulation according to claim 19, in which the active particles are present in an amount of from 0.1 to 50% by weight, based on the total weight of active particles and fine excipient particles.

21. A formulation according to claim 1, which contains up to 20% by weight of active particles, based on the total weight of the formulation.

22. A formulation according to claim 1, which comprises at least 50% by weight carrier particles, based on the total weight of the formulation.

23. A formulation according to claim 22, which comprises at least 70% by weight carrier particles, based on the total weight of the formulation.

24. A formulation according to claim 1, wherein the fine excipient particles are present in an amount of from not less than 5% by weight based on the total weight of the formulation up to 20% by weight based on the total weight of the formulation.

25. A formulation according to claim 24, in which the fine excipient particles are present in an amount of from not less than 5% by weight based on the total weight of the formulation up to 15% by weight based on the total weight of the formulation.

26. A formulation according to claim 1, which contains at least 20% by weight, based on the total weight of the formulation, of particles of diameter less than 20 μm.

27. A formulation according to claim 1, in which the active particles comprise an agent having therapeutic activity when delivered into the lung.

28. A formulation according to claim 27, in which the active particles comprise a therapeutically active agent for the prevention or treatment of respiratory disease.

29. A formulation according to claim 1, in which the active particles comprise one or more active agents selected from β2-agonists, ipratropium bromide, steroids, cromones and leukotriene receptor antagonists.

30. A formulation according to claim 27, in which the active particles comprise a therapeutically active agent for systemic use.

31. A formulation according to claim 27, in which the active particles comprise one or more agents selected from peptides, polypeptides, proteins and DNA fragments.

32. A formulation according to claim 31, in which the active particles comprise insulin.

33. A formulation according to claim 1, comprising more than 5% by weight, based on the total weight of the formulation, of particles of aerodynamic diameter less than 20 μm, the formulation having a flowability index of 12 mm or less.

34. A formulation according to claim 33, which comprises more than 10% by weight particles of aerodynamic diameter less than 20 μm.

35. A formulation according to claim 1, comprising:

from 5 to 90% by weight carrier particles having a diameter of at least 50 μm and a mass median diameter of at least 175 μm;

from 0.01 to 80% by weight of a therapeutically active agent;

from 9 to 50% by weight of particles of fine excipient material;

in each case, by weight, based on the total weight of the carrier particles, active agent and fine excipient material.

36. An inhaler device comprising a formulation according to claim 1.

37. A device according to claim 36, which is a dry powder inhaler.

38. A device according to claim 37, which is a pressurised metered dose inhaler.

39. A method of manufacturing a formulation according to claim 1, comprising mixing the fine excipient particles with the carrier particles and the active particles.

40. The formulation of claim 1 which has a flowability index of 12 mm or less.

41. The formulation of claim 1, wherein each carrier particle contains at least three lactose primary crystals of the tomahawk shape.

42. A formulation as claimed in claim 1, wherein the crystals of the agglomerate are fused to one another by solid bridges.

* * * * *